United States Patent [19]

Yarar et al.

[11] Patent Number: 4,939,458

[45] Date of Patent: Jul. 3, 1990

[54] METHOD AND APPARATUS FOR QUANTIFYING SUPERCONDUCTIVITY

[75] Inventors: Baki Yarar, Golden; Herbert R. Bird, Arvada, both of Colo.

[73] Assignee: Colorado School of Mines, Golden, Colo.

[21] Appl. No.: 153,208

[22] Filed: Feb. 8, 1988

[51] Int. Cl.$^5$ .................. G01N 27/72; G01R 33/12
[52] U.S. Cl. ............................ 324/228; 324/226; 324/235; 505/726; 505/842; 73/862.61
[58] Field of Search ............... 73/862.61; 324/228, 324/99 R, 235; 505/842, 726

[56] References Cited

U.S. PATENT DOCUMENTS 2,946,948 7/1960 Foner .
3,431,489 3/1969 Bridges .
3,609,526 9/1971 Chaberski .
3,976,934 8/1976 Voigt .

FOREIGN PATENT DOCUMENTS 1275780 8/1968 Fed. Rep. of Germany .... 324/99 R

OTHER PUBLICATIONS

Moon: "Hysteretic Levitation Forces in Superconducting Ceramics", Appl. Phys. Lett., May 2, 1988.
Barsoum: "Use of the Meissner Effect to Separate, Purify and Classify SC Ponders", Appl. Phys. Letters., Dec. 7, 1987.
Hellman "Levitation of a Magnet Over a Flat Type II SC", Bell Labs Tech. Report, Sep. 1987.

Primary Examiner—Reinhard J. Eisenzopf
Assistant Examiner—Jose M. Solis
Attorney, Agent, or Firm—Edwin L. Spangler, Jr.; Richard W. Hanes

[57] ABSTRACT

The invention relates to a novel apparatus for detecting as well as quantifying superconductivity characterized by a rigid-stemmed pendulum used to support the superconductive sample for free-swinging movement about a low-friction fulcrum in a magnetic field effective to swing the pendulum to one side, connecting both a first mechanism to the pendulum operative to sense the movement of the pendulum and generate a signal proportional thereto along with a second mechanism effective to receive such a signal from the first mechanism and react thereto in a manner to null the movement of the pendulum along with the sample suspended therefrom, and, finally, connecting a signal processing mechanism into the system whereby the signal generated by the first mechanism is quantified as a measure of the superconductive properties of the sample. The invention also encompasses the method for detecting and quantifying the superconductive properties of a purportedly superconductive sample which includes suspending the sample from a rigid-stemmed pendulum within a magnetic field effective to repel same when exhibiting the Meissner Effect, detecting the repelling force tending to swing the pendulum and measuring it as a quantification of the Meissner Effect force present in the superconductive sample, and nulling the swing of the pendulum by applying an oppositely-acting force thereto equal to the repelling force.

9 Claims, 1 Drawing Sheet

METHOD AND APPARATUS FOR QUANTIFYING SUPERCONDUCTIVITY

BACKGROUND OF THE INVENTION

While so-called "superconductive" materials have been known for many years, they were impractical as electrical conductors because of the necessity of keeping them at kryogenic temperatures approaching absolute zero. Very recently, however, renewed interest in superconductivity has arisen due to the fact that certain materials, most often alloys or mixtures of more than one substance, have been found that exhibit superconductive properties at much higher temperatures which are well within the realm of practical operating environments, if not for humans, certainly for machines.

Superconductive materials exhibit diamagnetic properties and a diamagnetic material is repelled by a magnet. When such a superconductive material is thus repelled, it is known as exhibiting the so-called "Meissner Effect". A superconductive material, of course, does not exhibit the Meissner Effect at all temperatures, but only at its critical temperature or below. At temperatures above its critical temperature, superconductive materials demonstrate the same properties as the same material or mixture of materials do at normal temperatures.

Accordingly, one sought-after piece of information concerning superconductive material or those suspected of being superconductive is to determine, if possible, the critical temperature at which they become superconductive. Also, when comparing superconductive materials, there is a need for a fast and reliable way of quantifying the superconductivity of two or more different samples, perhaps of the same or, alternatively, of different, materials. There may even be other properties apart from the mixture itself that effect the superconductivity or the lack thereof in certain substances such as, for example, grain size etc., and a reliable way of quantifying or even determining the existence of the Meissner Effect will tell much about these elusive properties.

FIELD OF THE INVENTION

The field of the present invention, therefore, is that of a method and apparatus for not only detecting superconductivity but quantifying it.

DESCRIPTION OF THE RELATED ART

The traditional methods used in measuring the susceptibility of weakly magnetic substances can be found at pages 74 through 78 of the textbook by B. D. Cullity entitled "Introduction to Magnetic Materials" (Addison-Wesley, Reading Mass. 1972) where the author describes two different systems, one the so-called "Faraday Method" and the other the "Gouy Method" for making susceptibility measurements. Both of the foregoing are known as "Force Methods", the latter consisting of the measurement of the force acting on a body when it is placed in a non-uniform magnetic field. The instrument designed to make such measurements is called a "magnetic balance".

Both of these methods involve the use of a sensitive beam balance from which the specimen is suspended in a magnetic field. The apparent increase in mass of the specimen as the field is turned on can be quantified and expressed in the customary units of force, dynes. Both of these methods are time-consuming and laborious.

The Gouy Method, while somewhat simpler than the Faraday Method, requires a very large sample. The Faraday Method, on the other hand, is characterized by the author as not being a good absolute method because of the difficulties associated with determining the field and its gradient at the position of the specimen. Both methods, it appears, require that measurements be taken over an extended temperature range to be of value in determining the true magnetic nature of the specimen and the furnaces and cryostats needed for such determinations must be narrow enough to fit into the magnetic gap and still be large enough to hold the specimen.

The weighing art includes an assortment of balances which provide for nulling the movement of the beam and quantifying the nulling force as a measure of the weight of the sample. So far as applicants are aware, however, the object being weighed is not subject to a magnetic field even though it might be composed of a magnetic or diamagnetic material. Even more significant is the fact superconductive materials possess unique properties all their own which must be dealt with knowledgeably and constructively in order to detect and quantify their Meissner Effect. The prior art relating to the nulling of balances and other systems has not to applicants' knowledge dealt in any way with these properties and problems peculiar to superconductive materials.

By way of example, the Bridges et al U.S. Pat. No. 3,431,489 deals with a nullable system that even includes a pendulum. It, however, it totally unsuitable for measuring the Meissner Effect of a superconductive sample. First of all, the sample sits within a coil which is, in turn, within a magnetic field. This field must, of necessity be very carefully constructed, aligned and configured. In other words, their null coil 13 and the gradient coils 23 and 24 which are excited by alternating current must be so configured that they have a frequency substantially equal to the mechanical resonating frequency of the pendulum. Applicants' system has no such complex field requirement but instead only that of superimposing a magnetic field on the superconductive specimen sitting in a holder. It requires no alternating currents or fields of fluxes, no null coil or gradient coils. Moreover, the sample never moves as it must do in the Bridges et al system in order to generate the curve of FIG. 4. In this prior art system, therefore, motion is essential while in the one forming the subject matter of the instant invention, no motion of the sample takes place and, as a matter of fact, the novelty of the system depends on the very fact that it does not move. Last but by no means least is the fact that systems such as that of Bridges et al are totally unsuited to the quantification of the Meissner Effect in superconductive materials that need to be cooled before they become superconductive which, up to the present time at least, is a requirement although not to the degree of cooling heretofore felt necessary. In any event, the field profile shown in FIG. 4 of the Bridges et al patent will change with temperature and thus introduce further complexities. Once again, applicants require no such uniform temperature and their system will work just as well while the temperature is going up and down as it will while it remains constant. Accordingly, while many systems of one type or another exist in the prior art where nulling takes place and is used to quantify some unknown such as weight, to applicants' knowledge, none of them are applicable to superconductive systems for measuring the Meissner Effect and even is such systems could be so used, they are far more complex, time-consuming and expensive than theirs.

By far the most pertinent prior art known to applicant is contained in a brief digest describing work being carried out at Fermi National Accelerator Laboratories found on page 5 of the Nov. 16, 1987 issue of a publication entitled "Superconductor Week". This digest describes a pendulum test for superconductor samples wherein a basket containing the sample is suspended from a four meter long thread. While the disclosure does not go into any detail whatsoever, presumably, the sample thought to be superconductive is first cooled down to a point where it exhibits superconductive properties and thereafter subjected to a magnetic field where, one suspects, the angle through which the pendulum swings is taken as a quantitative measure of the extent of the Meissner effect it exhibits.

SUMMARY OF THE INVENTION

It has now been found in accordance with the teaching of the present invention that a relatively simple, yet unobvious, combination of known components can be assembled by means of which one can almost instantly quantify the Meissner effect demonstrated by a sample of superconductive material once it has been cooled down to its critical temperature. The system will not only detect superconductivity but, in addition, show the critical temperature at which it becomes superconductive. The superconductivity of the sample over a wide range of temperatures during which it remains superconductive is easily determined as is the effect, if any, that changing the strength of the magnetic field has on its diamagnetic properties. As a matter of fact, it is very easy to continuously plot in real time the sample's Meissner effect strength as it reaches its critical temperature and is cooled further.

It is, therefore, the principal object of the present invention to provide a much improved and very simple method and apparatus for not only detecting that critical temperature at which a suspected superconductive material becomes superconductive but, in addition, quantifying its degree of superconductivity by measuring the Meissner effect it exhibits.

A second objective is that of providing an apparatus of the type aforementioned which can accommodate samples in solid, granular or even powdered form contained within a sample holder which, in turn, is immersed in a liquid or gaseous coolant.

An additional object is to provide a system and method of using same which continuously and instantaneously tracks the Meissner effect shown by a superconductive material.

Another objective of the within-described invention is that of quantifying the Meissner effect in terms of the strength of a nulling signal as opposed to having to read the angular deflection of a pendulum or attempt to measure a force acting upon the sample due to its presence in a magnetic field, the shape and strength of which are difficult to determine.

Still another object is to provide a method of determining the superconductive properties of mixtures of two or more superconductive materials having different critical temperatures.

Further objects are to provide a method and apparatus of the class described which has useful applications in quality control, quality assurance, purity control and as a research tool.

Other objects will be in part apparent and in part pointed out specifically hereinafter in connection with the description of the single figure of drawing which follows.

BRIEF DESCRIPTION OF THE DRAWING

The single FIGURE of drawing is a schematic representation of the apparatus used to determine a sample's superconductivity, if any; its critical temperature; and the magnitude of the Meissner effect exhibited thereby, all instantaneously and in real time.

DETAILED DESCRIPTION OF THE DRAWING

Figure 1:
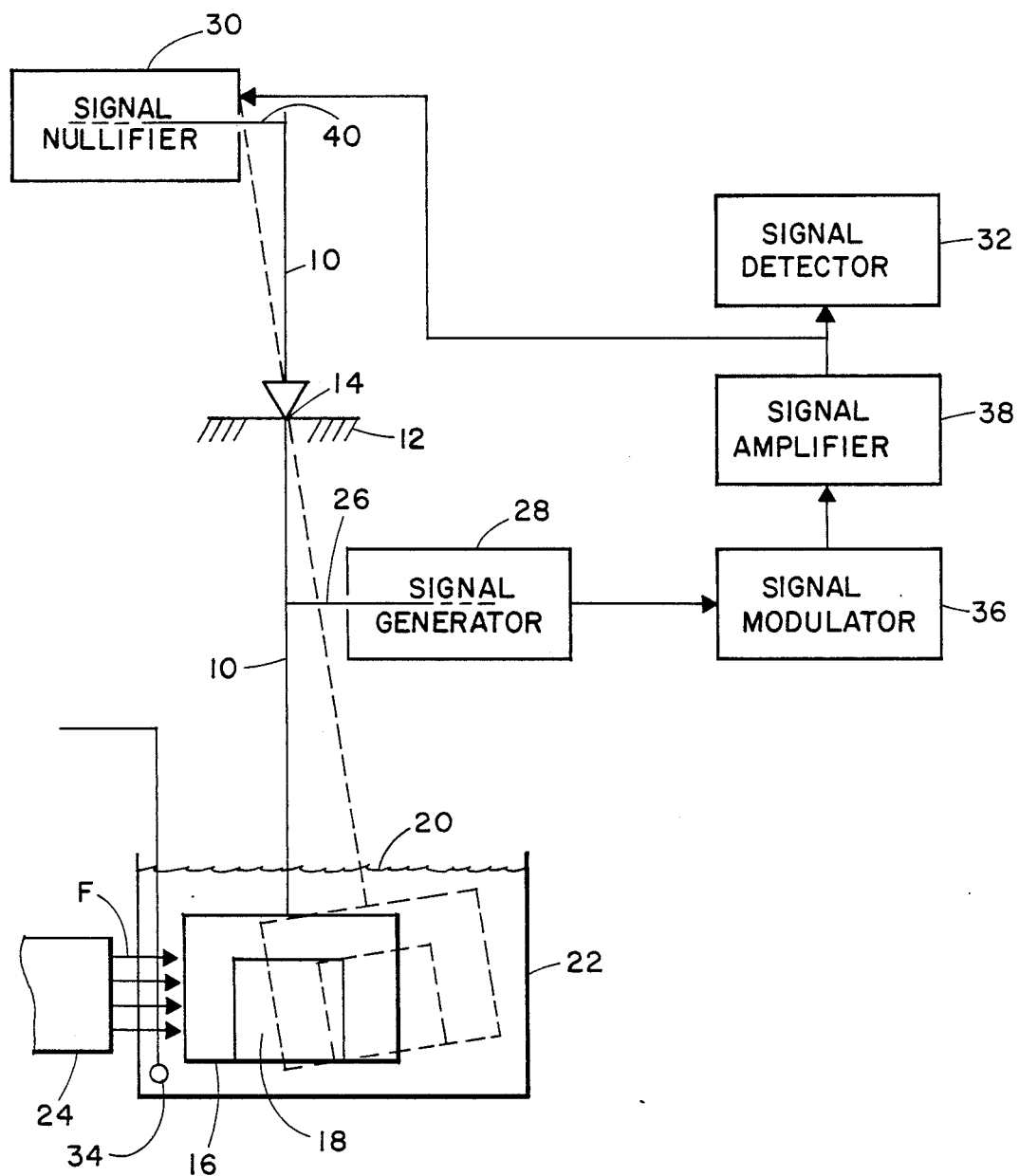

In the drawing, reference numeral 10 has been chosen to identify a pendulum which is suspended from a suitable support 12 to swing about a conventional low-friction fulcrum 14 positioned intermediate its ends. The lower end of the pendulum carries a sample holder shown in the form of a basket 16 into which is placed the sample 18 suspected to be superconductive. This sample may be a solid pellet or the like, be in granular form or even be powered. As a matter of fact, if superconductive liquids exist or, perhaps, minute superconductive particles suspended in a fluid, there is no reason they could not be tested in accordance with the teaching of the instant invention.

Up until the present time at least, no superconductive materials exist that do not have to be cooled to temperatures well below ambient conditions although these critical temperatures are certainly rising as new alloys and mixtures of materials are discovered. Assuming that the sample has to be cooled in order to reach its critical temperature, this can be accomplished outside the apparatus and then the sample thus cooled placed into the sample basket preparatory to investigating its superconductive properties. Obviously, this entails working rather rapidly before the sample warms up past its critical temperature and thus loses its superconductive properties. A far better and easier way is to immerse the sample basket 16 containing the sample 18 in a coolant medium of some type 20 contained within a coolant reservoir 22 as shown. It is important, however, that the sample basket not touch the bottom or the sides of the reservoir because if this were to occur, it would interfere with the free swing of the pendulum. It is also necessary that both the sample basket and the coolant reservoir be magnetically inert, i.e. unaffected by the magnetic field F generated by the source of magnetic energy 24 placed outside the reservoir but in close proximity to the sample.

The source of magnetic energy can be a permanent magnet, an electromagnet or, for that matter, any generator of a magnetic field F. Preferably, however, the source of magnetic energy should have a variable input such that the force field generated thereby can be increased or decreased in magnitude. Once the sample 18 reaches its critical temperature, being diamagnetic, it will be repelled by force field F and thus tend to move into the phantom-line position from its full-line "at rest" position through an angle (theta). For purposes of illustration, the angle (theta) has been grossly exaggerated since it may be only a degree or two and, for this reason, very difficult to measure accurately. This is the reason, undoubtedly, that the Fermi Laboratory group found it necessary to use a thread some four meters in length. If the thread were much shorter, the angle (theta) would likely become next to impossible to read with any semblance of accuracy.

There are, in addition, a number of other problems associated with allowing the sample to be deflected out of its position at rest. Obviously, one such problem is that the forces acting upon the sample which has swung through an arc no matter how small, must be resolved into vertically-acting ones and horizontal-acting ones in order to determine the resultant sidewise force exerted by the magnetic field. In addition, there are certain frictional forces acting upon the sample tending to retard its movement, most especially if it is immersed in a liquid coolant. All in all, the complexities resulting from trying to figure out the Meissner Effect upon a superconductive sample that has been allowed to move under the influence of a force field are quite significant. Moreover, even using sophisticated measuring devices such as lasers, optical interferometers and the like to measure the angle (theta), the resulting quantitative assessment of the sample's Meissner Effect will be approximate at best.

It has now been found in accordance with the teaching of the instant invention that these and other shortcomings of the prior art techniques for quantifying the Meissner effect can be eliminated by the simple, yet unobvious, expedient of not letting the sample leave its at rest position, but instead, sensing the Meissner Effect force it exerts in the presence of the magnetic field and impressing upon the pendulum a counteractive force of a magnitude which exactly balances and offsets the repelling force. By thus "nulling" the Meissner Effect force, the sample stays in place, the vertical and horizontal forces acting thereon do not have to be resolved, and the frictional forces acting upon the sample and its suspension do not come into play at all.

Sensing the Meissner Effect repelling force and nulling it can be accomplished in many ways. Broadly speaking, the system must include some means 26 responsive to the movement of the pendulum and a signal generator 28 sensitive to this movement and operative to generate a signal proportional to the repulsive force generated in the sample that tries to take it out of the magnetic field F. In other words, the force tending to move means 26 is an accurate measure of the Meissner Effect force exerted by the superconductive sample 18 as it tries to escape the magnetic field and if the signal generator 28 is capable of sensing the magnitude of this force and generating a signal proportional thereto, then the means is at hand for nulling the repelling force and quantifying it. Sidestepping for the moment the customary signal processors, the signal generated at 28 is fed to what has been denominated here a "signal nullifier" 30 which is operative to produce a signal of its own of equal magnitude to the one it has received but acting in the opposite direction, whereupon, this "null" signal is impressed upon the system to return the sample to its at rest position. Actually, of course, these offsetting signals counteract one another instantaneously so that there is really no movement of the sample at all.

The last element in the system is a signal detector 32 which reads either the null signal from signal nullifier 30 or the original signal from signal generator 28, both of which comprise quantitative measurements of the Meissner Effect repelling force exhibited by sample 18. If one wishes to compare the superconductive capabilities of two samples, he or she need only bring them down to their critical temperatures and measure their relative Meissner Effect forces measured in terms of constant level force field F. By adding a thermometer 34 to the system, it becomes possible to determine instantly a given substance's critical temperature. Also, if, for example, purity of the sample is a factor determinative of its superconductivity or lack thereof, the system provides a way of determining instantaneously whether a particular sample falls in the "good" or "bad" category. The addition of a thermometer gives the investigator the means by which he or she can analyze a sample having two or more superconductive materials in it, each having a different critical temperature.

By way of specific example of an apparatus which will function in accordance with the method of quantifying the Meissner Effect exhibited by a superconductive sample, the means 26 responsive to the movement of the sample under the influence of the magnetic field can be a simple ferrite rod. This rod enters signal generator 28 which takes the form of a linear, variable differential transformer which senses the motion of the ferrite rod 26 and generates a signal proportional to its movement. This signal, in the particular form shown, is then sent to a signal modulator 36 of conventional design and it, in turn, sends the signal thus modulated to a signal amplifier 38. The amplified signal is then sent primarily to the signal nullifier 30 which generates an equal and opposite "null" signal which it impresses upon a soft iron or ferrite core or moving coil or pivoted coil such as those found in a D'Arsonval Galvanometer or pivoted-coil galvanometer that is attached to the pendulum 10 above its fulcrum 14 in the particular form shown, whereupon, rod 40 activates the pendulum returning rod 26 to its original position thus compensating for any signal in signal generator 28. This amplified signal is also sent to the signal detector 32 which can take a number of different forms. For example, it can be a voltmeter, ammeter, galvanometer, a computer interface, a chart recorder or, frankly, all of the above. A voltmeter/ammeter combination could, if desired, be used in place of the aforementioned pivoted or moving coils as the signal nullifier 30.

An alternative set up, and one well within the skill of the art, would be to have element 26 be a linearly-movable shutter which, as it moves with the pendulum in response to the movement of the sample, begins to shut off light from a source thereof impinging upon a photocell in signal generator 28. As the photocell sees less and less light, it generates a signal of changing magnitude which instantaneously reaches the signal nullifier and the latter reacts by generating an equal and opposite signal transmitted to a mechanical device connected either to the pendulum or to the shutter mechanism 26 that is effective to haul it back and let the amount of light originally reaching the photocell reach same again.

Capacitative devices predicated upon the principle of the capacitance varying as the sensor responsive to movement of the pendulum changes the its position and thus invokes a response capable of producing the nulling signal, are also well within the skill of the artisan versed in electronics. The actual signal nullifier used in the system consisted of a pivoted-coil salvaged from a commercially-available galvanometer. It is not, therefore, the details of the individual components making up the system by means of which the Meissner Effect force is sensed, quantified and counteracted that constitutes the novelty present in the instant invention, but instead, the concept by which the magnitude of this force is measured and nulled such that no actual movement of the sample takes place, yet, an extremely accurate quantification of the Meissner Effect force generated by the superconductive material results and can be tracked, recorded and analyzed in real time substantially instantaneously.

Before leaving the drawing it should be noted that, as illustrated, the lengths of the lever arms of the pendulum extending above and below the fulcrum are of unequal length; however, this has no effect on the particular operations the system performs. For example, in making comparative measurements for quality assurance and product monitoring purposes, it can be used as is. On the other hand, when used for the determination of absolute Meissner Effect values, it will have to be calibrated with respect to a reference material. Thus, in either of these modes, the differences, if any, in the relative lengths of the pendulum lever arms becomes a matter of no consequence.

The unique method for quantifying the Meissner Effect repelling force generated by a superconductive material placed in a magnetic field in accordance with the teaching of the instant invention is, of course, first using a pendulum-type sensor from which the sample is suspended to sense the magnitude of the repelling force, generating an equal and opposite force effective to return the pendulum to its original position to keep the pendulum and sample from moving and, finally, measuring the magnitude of the repelling force.

It is also, perhaps, worthy of mention that, insofar as applicants are presently aware, no superconductive materials have yet been discovered which do not have to be cooled to some degree before they reach their critical temperatures. Nevertheless, the time may well come when substances which become superconductive at ambient temperatures or even when heated will be discovered. If this should occur, applicant's method and apparatus for detecting and quantifying the property of superconductivity in such materials is fully operable.

What is claimed is:

1. The apparatus for detecting and quantifying superconductivity which comprises: a pendulum having a rigid shaft mounted for pivotal movement between an at rest position and displaced positions to one side or the other of said at rest position, non-magnetic means for carrying a sample suspended from the pendulum for pivotal movement therewith, a source of magnetic energy positioned alongside said sample-carrying means adapted to repel a superconductive sample contained therein and move same in a superconductive state from its at rest position to a displaced position, first means carried by said pendulum responsive to movement of said sample from its at rest position into a displaced position, means responsive to the movement of said first means operative to generate a displacement signal proportional to the repelling force moving said sample to its displaced position, second means connected to said pendulum positioned and adapted upon actuation to move the latter in a direction opposite to that of said first means, means responsive to said displacement signal for generating a nulling signal of equal magnitude, means responsive to said nulling signal operative to act upon said second means and return said sample to its at rest position, and means connected to receive said displacement signal for quantifying same.

2. The apparatus for detecting and quantifying superconductivity as set forth in claim 1 which includes: means associated with the sample for indicating the temperature at which it becomes superconductive.

3. The apparatus for detecting and quantifying superconductivity as set forth in claim 1 which includes: means comprising a coolant reservoir for cooling the sample to the temperature at which it becomes superconductive.

4. The apparatus for detecting and quantifying superconductivity as set forth in claim 1 in which: the sample-carrying means comprises an immersible basket.

5. The apparatus for detecting and quantifying superconductivity as set forth in claim 1 in which: the source of magnetic energy has a variable output.

6. The apparatus for detecting and quantifying superconductivity as set forth in claim 3 in which: the coolant reservoir contains a coolant effective to cool the sample at least to a temperature at which it becomes superconductive, and in which the sample-carrying means is immersed in said coolant out of contact with said coolant reservoir.

7. The method for detecting and quantifying superconductivity which comprises the steps of: hanging a sample of superconductive material from a rigid-stemmed pendulum in a state of equilibrium, cooling the sample to a temperature at least as low as that at which it becomes superconductive, maintaining said sample in a state of superconductivity while placing it in a magnetic field effective to repel same and move it from its equilibrium position, impressing a force upon said pendulum effective to return it together with the sample suspended therefrom to their equilibrium position, and measuring magnitude of the force thus impressed.

8. The method for detecting and quantifying superconductivity as set forth in claim 7 which includes the steps of: cooling the sample to a temperature at which it becomes superconductive and recording said temperature.

9. The method for detecting and quantifying superconductivity as set forth in claim 7 which includes the steps of: immersing the sample in a coolant while isolating said sample from the vessel containing same.

* * * * *